United States Patent [19]

Terayama et al.

[11] Patent Number: 4,820,837

[45] Date of Patent: Apr. 11, 1989

[54] 1-HYDROXY-OXO-5H-PYRIDO(3,2-A)PHENOXAZINE-3-CARBOXYLIC ACID ESTERS

[75] Inventors: Hideo Terayama, Itami; Jun Inoue, Settsu, both of Japan

[73] Assignee: Senju Pharmaceutical Co., Ltd., Osaka, Japan

[21] Appl. No.: 68,159

[22] Filed: Jun. 30, 1987

[30] Foreign Application Priority Data

Jul. 15, 1986 [JP]  Japan .................................. 61-166066

[51] Int. Cl.$^4$ ............................................ C07D 498/04
[52] U.S. Cl. ............................................................ 544/99
[58] Field of Search ................ 544/99; 514/236, 299.5

[56] References Cited

U.S. PATENT DOCUMENTS 4,092,410  5/1978  Ogata et al. ...................... 544/99 X
4,233,305  11/1980  Allais et al. ..................... 514/236 X
4,369,184  1/1983  Stokbroekx et al. ............ 514/236 X Primary Examiner—Richard L. Raymond
Attorney, Agent, or Firm—Wenderoth, Lind & Ponack

[57] ABSTRACT

The compounds represented by the general formula

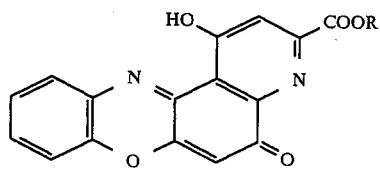

wherein R is an alkyl group having 1-10 carbon atoms are novel compounds which have not been reported in the literature. Since they have excellent affinities for tissues with particular high corneal permeability and show anticataract activity at low concentration, the compounds are of value as prophylactic and therapeutic agents for cataracts.

5 Claims, No Drawings

1-HYDROXY-OXO-5H-PYRIDO(3,2-A)PHENOXAZINE-3-CARBOXYLIC ACID ESTERS

BACKGROUND OF THE INVENTION

1. Field of the Invention

The present invention relates to a novel and useful phenoxazine derivative having prophylactic and therapeutic effects on cataracts, a process for production thereof, and an anticataract composition containing said phenoxazine derivative.

2. Description of the Prior Art

While cataracts is a disease arising from opacification of the lens, its pathogenesis remains to fully elucidated as yet. It follows, then, that a prophylactic and therapeutic pharmacotherapy has not been established for the disease. Under the circumstances, 1-hydroxy-5-oxo-5H-pyrido[3,2a]phenoxazine-3-carboxylic acid and its salt have been accredited with the reputation of being the most effective of all the drugs available so far for cataracts, and are being used widely, particularly as agents for arresting the progression of early-stage senile cataracts, with successful results.

Under the circumstances, on the thought that the efficacy of these compounds might be enhanced if the rate of transfer of the compound to tissues be increased, the present inventors synthesized a series of compounds structurally related to the above known compounds and ultimately succeeded in the synthesis of ester derivatives meeting the above-mentioned objective. The present invention has been developed on the basis of the above accomplishment.

SUMMARY OF THE INVENTION

The present invention is directed to:
(1) a compound of general formula

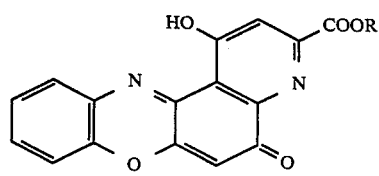

wherein R is an alkyl group having 1-10 carbon atoms;

(2) a process for producing a compound of general formula

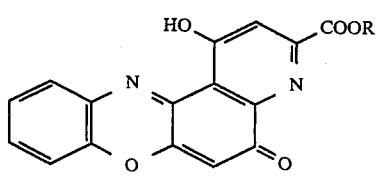

wherein R is an alkyl group having 1-10 carbon atoms characterized by esterifying a compound of general formula

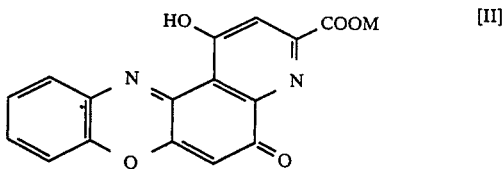

wherein COOM is a carboxyl group which is either free or in the form of a salt; and (3) an anticataract composition comprising a compound of general formula

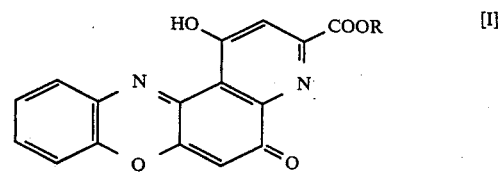

wherein R is an alkyl group having 1-10 carbon atoms.

DETAILED DESCRIPTION OF THE INVENTION

Referring to general formula [I], the alkyl group R is a straight-chain or branched alkyl group containing 1 to 10, preferably 1 to 8, carbon atoms, such as methyl, ethyl, propyl, isopropyl, butyl, isobutyl, sec-butyl, tert-butyl, pentyl, isopentyl, neopentyl, hexyl, isohexyl, heptyl, 5-methylhexyl, octyl and so on.

The compounds of general formula [I] are novel compounds which have not been reported in the literature. Being more lypophilic than compound [II], these esters are more readily transferred to various tissues and show high corneal permeability, in particular, and it displays sufficient anticataract activity at low concentration. Moreover, the ester [I] according to the present invention can be repeatedly administered.

In applying the compound of general formula [I] clinically as a drug, it can be administered parenterally or orally in various dosage forms such as granules, tablets, capsules, injections and so on. However, it is particularly suitable to administer the compound topically in the form of eye-drops or an ophthalmic ointment. In formulating the compound [I] into any of such pharmaceutical preparations, the pharmaceutical methods established for the respective dosage forms can be utilized.

The dosage of compound [I] depends on various factors such as kinds of ester, dosage form, disease condition and the patient's age and body weight. However, for oral administration to adult patients with cataracts, for instance, the compound can be administered in a daily dose of about 0.1 to 500 mg, preferably from about 1 to 100 mg, once a day or in a few divided doses a day.

For topical application, the compound [I] can be administered in the form of an ophthalmic solution or suspension (eye-drops) containing about 0.0001 to 1.0%, preferably about 0.001 to 0.1%, of compound [I] at the dosage level of one to a few drops per dose with a frequency of about 3 to 5 times per day. For application as an ophthalmic ointment, about 0.0001 to 1.0% and preferably about 0.0001 to 0.1% of the compound [I] can be formulated with an ophthalmic ointment base which is commonly employed and the resulting ointment be administered with a frequency of about 1 to 4 times according to the condition of the disease. Other medicinal substances may be incorporated in such pharmaceutical preparations in addition to the compound [I] according to the present invention, unless it is contrary to the object of the present invention.

The compound of general formula [I]

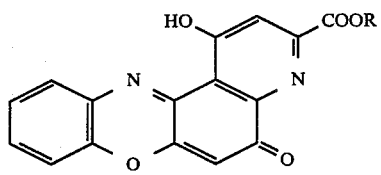

wherein R has the meaning defined hereinbefore can be produced by esterifying a compound of general formula

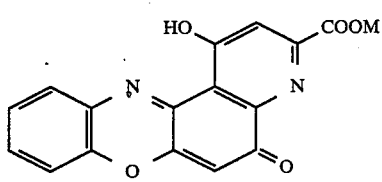

wherein COOM has the meaning defined hereinbefore.

The compound of general formula [II] can be prepared by various methods, for example by the processes described in Japanese Examined Patent Publication No. 34-2227 and No. 36-7372.

The salts of compound [II] include the corresponding alkali metal salts (e.g. sodium, potassium), alkali earth metal salts (e.g. magnesium) and other salts.

The esterification of compound [II] may be accomplished by various alternative methods, e.g. the method in which the corresponding alcohol (ROH) and an acid (e.g. hydrogen chloride, sulfuric acid, p-toluéne-sulfonic acid, etc) are employed and the method in which an alkyl halide, an alkyl sulfonate, and alkyl sulfonate ester (e.g. alkyl toluenesulfonate, alkyl benzenesulfonate, alkyl methanesulfonate, etc.), a dialkyl sulfate or the like is used in the presence of a base. Particularly preferred is the esterification method in which an alkyl halide is used in the presence of an alkali carbonate (e.g. potassium carbonate, sodium carbonate, etc.) in a solvent such as dimethylformamide (DMF).

As the solvent, inert solvents (e.g. dimethylformamide, dimethyl sulfoxide, dimethoxyethane, methanol, ethanol, propanol, isopropyl alcohol, butanol) are advantageously used.

When the compound [II] is a free carboxylic acid, the esterification reaction is carried out in the presence of a base but this is not necessary when a salt of compound [II] is employed.

The esterifying agent is preferably an alkyl halide, in which the halogen may for example be chlorine, bromine or iodine.

This reaction generally can be conducted at about 20° to 150° C. and preferably at about 60° to 120° C. The amount of the base relative to each mole of free compound [II] is about 0.5 to 5 moles and preferably about 1 to 2 moles. The amount of the esterifying agent relative to each mole of free compound [II] is about 1 to 10 moles and preferably about 2 to 6 moles.

The following examples are further illustrative of the present invention.

EXAMPLE 1

(Production of the methyl ester of compound [I])

A mixture of 1.00 g 1-hydroxy-5-oxo-5H-pyrido[3,2-a]phenoxazine-3-carboxylic acid, 0.67 g finely divided potassium carbonate, 1.06 ml methyl iodide and 40 ml DMF was stirred with heating at 80° C. for 3 hours. After cooling, the reaction mixture was poured in icewater and made acidic with 2N-hydrochloric acid. The crystals that formed were collected by filtration and rinsed. The rinsed crystals were dissolved in chloroform and the solution was washed with aqueous sodium hydrogen carbonate solution and water in that order. The organic layer was taken and dried over magnesium sulfate, followed by distillation to remove the solvent. Ethanol was added to the residue and the crystals were recovered by filtration and recrystallized from chloroform-ethanol to give oragne-colored prisms: yield 0.78 g; m.p. 267° C. (decomp.);

NMR (CDCl$_3$)$\delta$: 4.10 (3H, s), 6.66 (1H, s), 7.25–7.80 (4H, m), 7.97 (1H, s), 13.64 (1H, s; exchangeable); IR (KBr)$\nu$: 1710, 1645, 1585 cm$^{-1}$.

Elemental analysis: Calcd. H, 3.11; C, 63.35; N, 8.70; Found H, 3.08, C, 63.22, N, 8.51.

EXAMPLE 2

(Production of the ethyl ester of compound [I])

The procedure of Example 1 was repeated except that 1.30 ml of ethyl iodide was used in lieu of methyl iodide to give orange-colored prisms: yield 0.68 g; m.p. 284° C. (decomp.);

NMR (CDCl$_3$)$\delta$: 1.46 (3H, t), 4.51 (2H, q), 6.63 (1H, s), 7.2–7.85 (4H, m), 7.94 (1H, s), 13.6 (H, s; exchangeable); IR (KBr)$\nu$: 1763, 1655, 1595 cm$^{-1}$.

Elemental analysis: Calcd. H, 3.57; C, 64.29; N, 8.33; Found H, 3.49; C, 64.00; N, 8.13.

EXAMPLE 3

(Production of the butyl ester of compound [I])

The procedure of Example 1 was repeated except that 1.50 ml of butyl iodide was used in lieu of methyl iodide to give orange-colored prisms: yield 0.99 g; m.p. 295° C. (decomp.);

NMR (CDCl$_3$)$\delta$: 1.00 (3H, t), 1.39–1.58 (2H, m), 1.77–1.91 (2H, q), 4.45 (2H, t), 6.63 (1H, s), 7.2–7.8 (4H, m), 7.94 (1H, s), 13.6 (H, s; exchangeable; IR (KBr)$\nu$: 1765, 1655, 1593 cm$^{-1}$;

Elemental analysis: Calcd. H, 4.40; C, 65.93; N, 7.69; Found H, 4.39; C, 65.73; N, 7.48.

EXAMPLE 4

(Production of the isopropyl ester of compound [I])

The procedure of Example 1 was repeated except that 1.995 g of isopropyl bromide was used in lieu of methyl iodide together with 1.121 g of potassium carbonate to give orange-colored prisms: yield 0.81 g; m.p. 283°–286° C. (decomp.);

NMR (CDCl$_3$)$\delta$: 1.45 (6H, d), 5.2–5.5 (1H, m), 6.66 (1H, s), 7.26–7.79 (4H, m), 7.94 (1H, s), 13.65 (1H, s); IR (KBr)$\nu$: 1748, 1645, 1580 cm$^{-1}$;

Elemental analysis: Calcd. H, 4.03; C, 65.14; N, 8.00; Found H, 4.08; C, 65.22; N, 8.01.

EXAMPLE 5

(Production of the heptyl ester of compound [I])

The procedure of Example 1 was repeated except that 2.905 g of heptyl bromide was used in lieu of methyl iodide to give orange-colored prisms: yield 0.68 g; m.p. 277°-279° C. (decomp.); NMR (CDCl$_3$)δ: 0.75-1.00 (3H, m), 1.15-1.60 (8H, m), 1.65-2.05 (2H, m), 4.43 (2H, t), 6.60 (1H, s), 7.20-7.80 (4H, m), 7.90(1H, s), 13.60 (1H, s); IR (Kbr)ν: 1740, 1635, 1560 cm$^{-1}$;

Elemental analysis: Calcd. H, 5.46; C, 67.97; N, 6.89; Found H, 5.47; C, 68.01 N, 7.02.

EXAMPLES 6-8

The procedure of Example 1 was repeated except that methyl sulfonate, methyl toluenesulfonate or dimethyl sulfonate was used in lieu of methyl iodide to give methyl ester of compound [I].

The following pharmaceutical preparation examples are further illustrative of the present invention.

PREPARATION EXAMPLE 1

Ophthalmic solution
Methyl ester of the present invention 0.002 g
Boric acid 1.5 g
Borax q.s.
Polysorbate 80 0.5 g
Methyl p-hydroxybenzoate 0.0026 g
Propyl p-hydroxybenzoate 0.0014 g
Sterile pure water To make the total amount 100 ml (1) Methyl p-hydroxybenzoate and propyl p-hydroxybenzoate were dissolved in 80 ml of sterile pure water under warming, and the solution was cooled.

(2) To the solution obtained in (1) were added boric acid, Polysorbate 80 and methyl ester, and the mixture was dissolved.

(3) Boric acid was added to the solution obtained in (2) and the pH of the mixture was adjusted to 6.0. Then sterile pure water was added to make the total amount 100 ml and the mixture was filtered and sterilized through a 0.22 μm membrane filter.

(4) An ophthalmic dispenser-container was filled aseptically with the solution obtained in (3).

PREPARATION EXAMPLE 2

Ophthalmic ointment
Ethyl ester of the present invention 0.005 g
Liquid paraffin 1 g
White petrolatum To make the total amount 100 g The above components were mixed in the routine manner to prepare an ophthalmic ointment.

PREPARATION EXAMPLE 3

Ophthalmic ointment
Heptyl ester of the present invention 0.005 g
Liquid paraffin 1 g
White petrolatum To make the total amount 100 g The above components were mixed in the routine manner to provide an ophthalmic ointment.

PREPARATION EXAMPLE 4

Ophthalmic suspension
Butyl ester of the present invention 0.005 g
Sodium dihydrogen phosphate.12H$_2$O 0.5 g
Sodium dihydrogen Phosphate.2H$_2$O 0.05 g
Sodium chloride 0.85 g
Polysorbate 80 0.2 g
Benzalkonium chloride 0.01 g
Sterile pure water To make the total amount 100 ml (1) To 80 ml of sterile pure water were added sodium dihydrogen phosphate.12H$_2$O, sodium dihydrogen phosphate. 2H$_2$O, sodium chloride, Polysorbate 80 and benzalkonium, and the mixture was dissolved. Then the solution was filtered and sterilized through a 0.22 μm membrane filter.

(2) Butyl ester was sterilized by heating under anhydrous conditions and then pulverized aseptically in an agate mortar.

(3) Pulverized butyl ester obtained in (2) was added to the solution obtained in (1), and the mixture was made into a suspension by using a homogenizer-mixer or an ultrasonicicator. Then sterile pure water was added to the suspension to make the total amount 100 ml.

(4) An Ophthalmic dispenser-container was filled aseptically with the suspension obtained in (3).

PREPARATION EXAMPLE 5

Oral tablets
Ethyl ester of the present invention 10 mg
Crystalline cellulose 100 mg
Hydroxypropylmethylcellulose 20 mg
Magnesium stearate 2 mg Mold the above components (regarded as quantities per tablet) into tablets.

We claim:

1. A compound of the formula

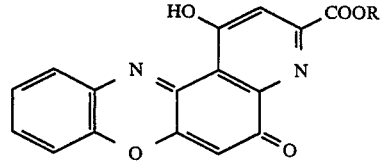

wherein R is. ethyl, propyl, isopropyl, or butyl.

2. The compound as claimed in claim 1, wherein R is an ethyl group.

3. The compound as claimed in claim 1, wherein R is an isopropyl group.

4. The compound as claimed in claim 1, wherein R is a butyl group.

5. The compound as claimed in claim 1 wherein R is a propyl group.

* * * * *